017# United States Patent [19]

Moller

[11] Patent Number: 4,579,658
[45] Date of Patent: Apr. 1, 1986

[54] FILTER ELEMENT

[76] Inventor: Klaus Moller, Baunegårdsvej 50 C, DK-2900 Hellerup, Denmark

[21] Appl. No.: 504,971

[22] Filed: Jun. 16, 1983

[51] Int. Cl.⁴ .............................................. B01D 27/08
[52] U.S. Cl. .................................... 210/483; 55/492; 604/333
[58] Field of Search ................ 55/484, DIG. 31, 491, 55/492, 529; 210/484, 485, 496, 497.01, 497.2, 503-509, 483, 495; 604/333

[56] References Cited

U.S. PATENT DOCUMENTS 2,175,195 10/1939 Irvine ........................... 55/DIG. 31
3,252,270 5/1966 Pall et al. ............................ 210/505
3,796,416 3/1974 Knudson ...................... 55/DIG. 31
4,331,148 5/1982 Steer et al. ........................... 604/333
4,460,394 7/1984 Wrightson .................... 55/DIG. 31

Primary Examiner—Ivars Cintins

[57] ABSTRACT

In a sheet-like filter element comprising a porous or fibrous filtering layer and a pair of opposite cover layers, these cover layers are maintained in tight engagement with the outer surfaces of the filtering layer by means of transversely extending connecting strings. The filter element may, for example, be used as a filter for a gas venting opening in a stoma bag, and in that case the porous filtering layer contains a big amount of finely granulated activated carbon. The connecting strings maintain the cover layers pressed against the filtering layer so as to avoid any tendency to delamination of the filtering layer and formation of undesired spaces or passages therein.

15 Claims, 10 Drawing Figures

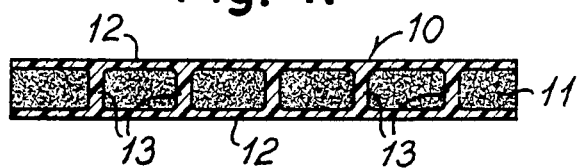
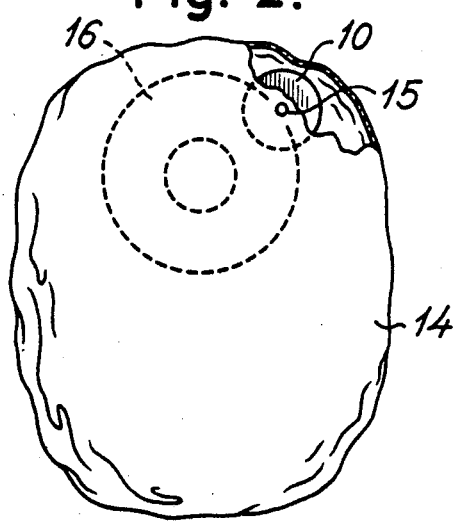
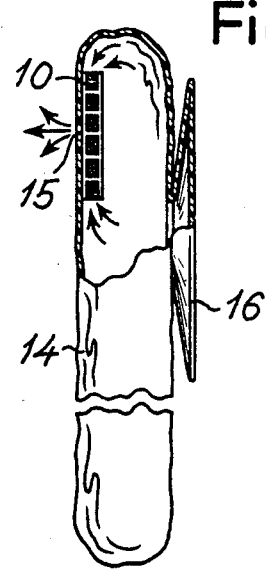
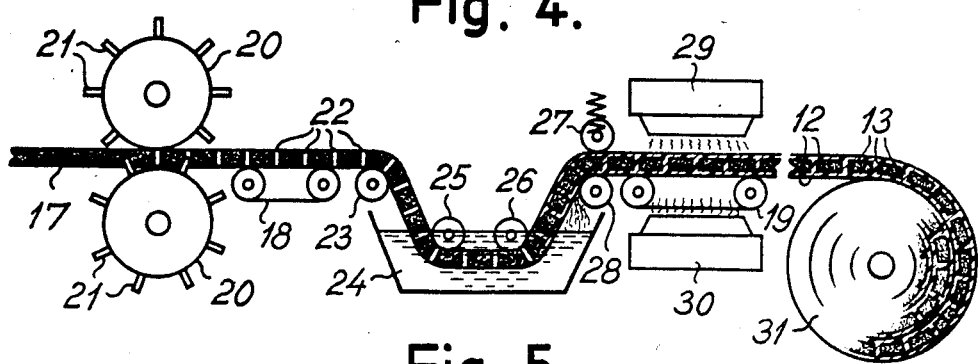
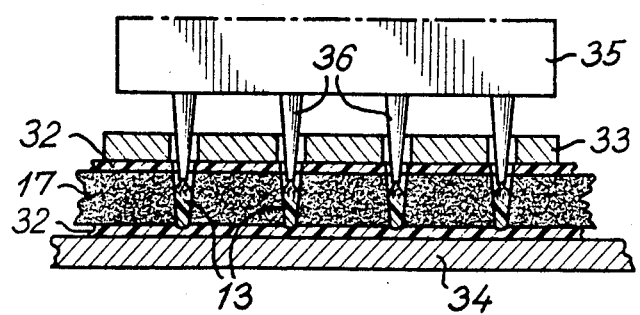

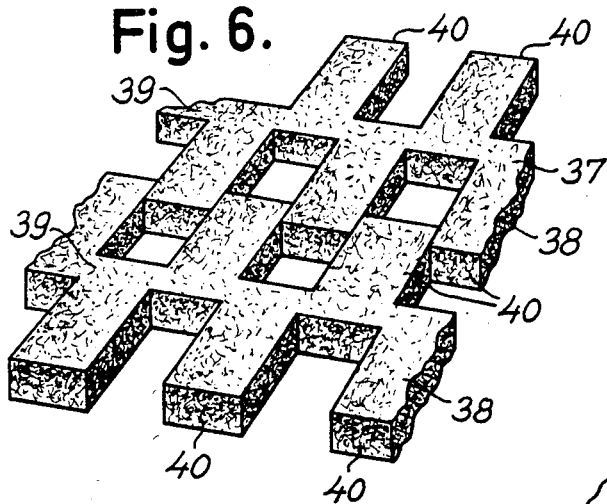
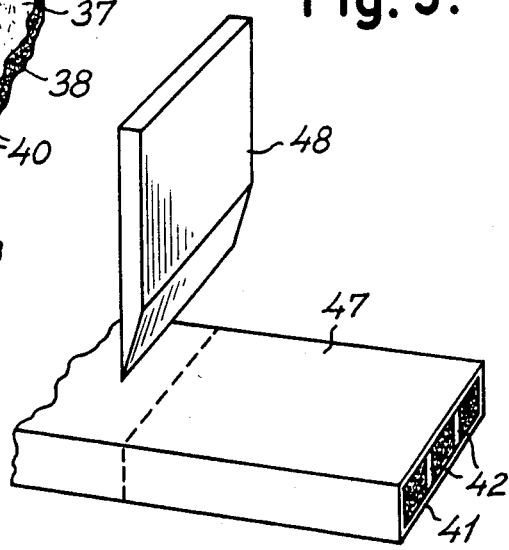
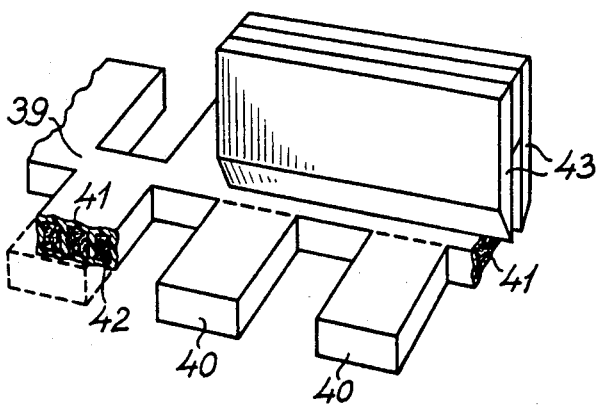
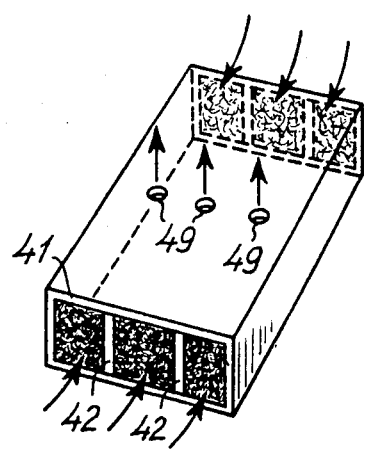
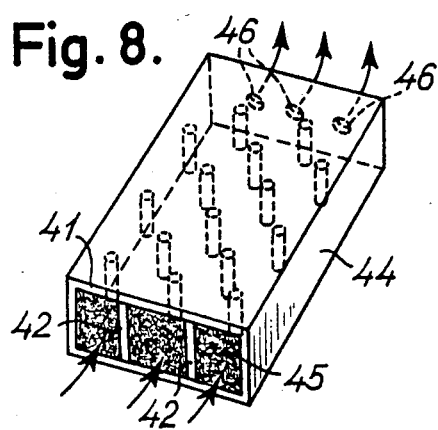

FILTER ELEMENT

BACKGROUND OF THE INVENTION

1. Field of the Invention

The present invention relates to a plate-like or sheet-like element for filtering a fluid flowing therethrough. Filter elements of this type may, for example, by used as a venting filter for stoma bags, which means collection pouches for receiving drainage from an abdominal opening following surgery. The filter element of the type in question may also be used in gas masks, as air inlet filter in combustion engines, and for several other purposes, where a liquid or gaseous fluid is to be filtered in order to remove solid particles and/or certain gaseous or liquid components therefrom.

2. Description of Prior Art

A filter element of the above type for use as a venting filter for stoma bags is disclosed in U.S. Pat. No. 3,759,260. This known filter element comprises a filter disc of matted fibers and granular activated carbon, and the filter disk is covered by and sandwiched between a pair of plastic sheets, which are sealed at the periphery of the disk. A central gas outlet opening is provided in one of the plastic sheets, and gas inlet openings are provided along the periphery of the disk. In this known filter element, the plastic sheets loosely engage with, but do not adhere to, the opposite side surfaces of the filter. German patent No. 613,113 discloses a filter element of the same type, where the plastic sheets adhere to the adjacent side surfaces of the filter disk by means of an adhesive, and the oppositely arranged plastic sheets are separated along the periphery of the filter element so that the filter disk, which is made from matted fibres and activated carbon enclosed therein, is exposed along the periphery thereof.

In the former known filter element, the gas flowing from the interior of an associated stoma bag tends to flow through passages defined between the filter disk and the adjacent plastic sheet, whereby the gas does not come into the intended intimate contact with the granulated carbon contained in the filter disc. In the latter known filter element, where the plastic sheets are glued to the adjacent opposite surfaces of the filter disk, the gases to be filtered are forced to flow through the mattet fibres, when passing radially through the filter.

However, the filtering or absorption capacity of a gas filter of the above type is to a high extent dependent on the amount of active substance, such as activated carbon, which is contained in each volume unit of the filter material sandwiched between the gas impervious cover sheets or plastic sheets, and, consequently, the minimum dimensions of a filter element of the type in question are dependent on the content of the active substance. The active substance, such as activated carbon, is embedded in a matrix formed by matted fibers. Normally, a high content of the activated carbon causes a reduction of the cohesion of the fibrous material, and in some cases the fibrous material even tends to delaminate. Therefore, even when the covering plastic sheets are glued to the adjacent surfaces of the filter disk, undesired flow passages may be formed in the fibrous material, whereby the gas flow through the filter element is not uniformly distributed, so that the efficiency of the filter is reduced. Furthermore, a high content of activated carbon or another active substance within the fibrous filter disk will normally make the gluening of the covering plastic sheets to the fibrous filter disk more difficult.

GENERAL DESCRIPTION OF THE INVENTION

The present invention provides a plate-like or sheet-like filter element of the above type, which may be used for several purposes, for example as a venting filter in stoma bags, and wherein the risk of delamination of the fibrous or porous filtering layer and of formation of undesired flow passages in the filter element is eliminated or substantially reduced, even when the fibrous or porous layer has a high content of an active substance, such as activated carbon.

Thus, the present invention provides a plate-like element for filtering a fluid flowing therethrough, said element comprising a filtering layer, including a deformable porous material, a pair of cover layers covering opposite side surfaces of the filtering layer and being of a material, which is substantially impervious to said fluid, and a plurality of spaced connecting strings extending transversely through the filtering layer and interconnecting said opposite cover layers. These connecting strings which are preferably closely spaced and uniformly distributed over the area of the filtering element, maintain the oppositely arranged cover layers in tight engagement with the adjacent surfaces of the filtering layer and also prevent or considerably reduce the risk of delamination of the filtering layer. In its presently preferred embodiment, the filtering element according to the invention is used for filtering gaseous fluid, such as venting gases from stoma bags, gases which are inhalated through gas masks, and the like. However, the filter elements according to the invention may also be used for the absorption of liquid fluids or components t hereof, such as urine, blood, and other body fluids. As indicated above, the filter element according to the invention may also be used for other filtering purposes, such as for filtering solid particles and/or gaseous and/or liquid components from gaseous or liquid fluids.

In order to further reduce the risk of delamination of the filtering layer, the connecting strings are preferably given a length, which is smaller than the thickness of the filtering layer in its released condition, whereby the filtering layer is maintained in a somewhat compressed condition.

In principle, the connecting strings may be of any suitable material, which is able to transfer the tensile forces corresponding to the forces desired for pressing the cover layer against the deformable filtering layer, which is preferably somewhat resilient. Like in the above mentioned known filter elements, the cover layers may be made from prefabricated plastic films or sheets, and the connecting strings may then be made from preformed strings or threads, which are passed transversely through the filter element and thereafter fastened to the cover layers with the desired tension, for example by welding.

However, it is desired to mould or form the connecting strings and preferably also the cover layers in situ. In this case, the connecting strings and/or the cover layers may be formed from a curable liquid plastic material.

The filter element according to the invention may have a circular shape like the known filter described above, and the radius of the element may exceed a multiple of the thickness of the filtering layer. The filter element may be provided with a centrally positioned opening defined in one of the opposite cover layers and one or more openings formed at the periphery of the element. The gas or liquid to be filtered may then flow from the periphery of the filter element radially to the central opening or in the opposite direction. The filter element may, alternatively, have an elongated shape. In that case openings may be provided so that the gas or liquid to be filtered flows longitudinally through the filter element from one end of the element to the other, or from central openings toward both ends of the element, or in the opposite directions.

The invention also provides a method of making the plate-like filter element for filtering a fluid, said method comprising applying fluid impermeable cover layers to opposite side surfaces of the filtering layer, which includes a deformable porous material, providing a plurality of spaced passages extending transversely through the filtering layer, filling said passages with a curable liquid substance, and curing said substance in said passages so as to form connecting strings extending transversely through the filtering layer and interconnecting said opposite cover layers. The cover layers may, for example, be prefabricated plastic films which are arranged on opposite sides of the filtering layer prior to forming the transversely extending passages. The passages may then be filled with the curable liquid substance by means of nozzles or spouts which are inserted into these passages, and which may possibly also be used for making these passages. However, it is preferred to apply at least one—and preferably both—of the cover layers to the respective side surface or surfaces of the filtering layer in a liquid state, and some of the liquid substance applied to the side surfaces may then be caused to penetrate into and fill the transverse passages. The filtering layer and the cover layers formed thereon will then form an integrated unit so that the risk of formation of undesired flow passages at the boundaries between the various layers and within the filtering layer due to delamination, is substantially eliminated, even when the filtering layer contains a relatively high amount of activated carbon or another active substance.

The curable liquid substance may be applied to the filtering layer in any suitable matter, for example by means of a roller, a spraying device, or a wiping device. However, the liquid substance is preferably applied to the filtering layer by dipping the layer into a bath of the liquid substance. The liquid substance may then be cured and solidified, for example by drying and/or heating, or by the interaction of a suitable chemical substance. The said liquid substance is preferably of a type, which shrinks during the curing treatment, whereby the desired compression of the filtering layer may be obtained.

BRIEF DESCRIPTION OF THE DRAWINGS

The invention will now be further described with reference to the drawings, wherein FIG. 1 is a diagrammatic sectional view of an embodiment of the filter element according to the invention, FIG. 2 is a front and partially sectional view of a stoma bag or collecting pouch, which is provided with a filter element as that shown in FIG. 1, but shown in a reduced scale, FIG. 3 is a side and partially sectional view of the stoma bag shown in FIG. 2, FIG. 4 illustrates a method of making a filter web, from which filter elements according to the invention may be punched, FIG. 5 illustrates an alternative method of making such a filter web, FIG. 6 is a perspective view showing partially separated blanks cut or punched from a web or layer of a filtering material, FIG. 7 illustrates how filtering elements may be cut from the blank, when a liquid plastic material has been applied thereto and cured, FIG. 8 is a perspective view of a filter element made by the method illustrated in FIGS. 6 and 7, FIG. 9 illustrates a further method of making filter elements according to the invention, and FIG. 10 is a perspective view of a filter element made by the method illustrated in FIG. 9.

DESCRIPTION OF THE PREFERRED EMBODIMENTS

FIG. 1 shows a plate-like or sheet-like filter element 10 including a fliltering layer 11, which may be formed by a porous, preferably fibrous matrix, which contains an active substance, such as granulated activated carbon, or another substance which is able to absorp or adsorb certain gaseous or liquid components. The opposite side surfaces of the filtering layer 11 are covered by gas impervious cover layers 12 of plastic material, and these cover layers are interconnected and kept in tight engagement with the filtering layer 11 by means of connecting strings 13, which extend transversely right through the filtering layer, and which are uniformly distributed over the area of the filter element 10.

The filter element 10 may, for example, be used as a venting filter in a stoma bag or collecting pouch 14 as that shown in FIGS. 2 and 3. As shown in FIGS. 2 and 3 the filter element 10 may be fastened to the inner side surface of the wall of the bag 14 and at the upper end thereof. In that case, a central outlet opening, which is aligned with a venting opening 15 in the adjacent wall of the stoma bag 14, is defined in one of the cover layers 12 of the filter element 10. The stoma bag 14 is also provided with an inlet spout 16 adapted to sealingly adhere to the skin of the patient around an abdominal or stoma opening.

From this stoma opening not only faecal matter, but also flatus may flow into the bag 14. As indicated by arrows in FIG. 3, flatus may flow continuously from the stoma bag into the filter element 10 along the peripheral edge thereof, and radially through the filtering layer 11 to the centrally arranged venting opening 15. While flatus passes the filtering layer 11 of the filter element 10, it comes into intimate contact with the activated carbon or another active substance, which is incorporated therein, and which absorbs the malodorous components of flatus. The connecting strings 13 ensure that the cover layers 12 are kept in tight engagement with the filtering layer 11, and that this filtering layer is not allowed to delaminate. Thus, any tendency to delamination and formation of undesired flow passages through the filtering layer 11 is eliminated, whereby the flow of flatus through the filter element 10 will distribute uniformly over the total peripheral cross-sectional area of the filtering layer. Consequently, the activated carbon or active substance incorporated in the filtering layer may be utilized more efficiently.

If desired, the filter element 10 may be fastened to the outer surface of the stoma bag 10, and flatus will then flow into the filter element through its central opening and then radially outwards in all directions. Such an embodiment has the disadvantages that the central inlet opening may more easily become blocked by faecal matter, which comes into contact therewith, than the peripheral gas inlet opening defined between the peripheral spaces of the cover layers 12 in the embodiment shown in FIGS. 2 and 3.

FIG. 4 illustrates a method of making a filtering web from which filter elements or plate-like elements of the type shown in FIG. 1 may be cut or punched. A web 17 of a fibrous material containing an active substance and adapted to form the filtering layer 11 of the finished plate-like or sheet-like filter element is moved by means of supporting conveyor belts 18 and 19. The web 17 is passed between a pair of cooperating drums 20, each of which is provided with a plurality of spikes 21, which extends radially outwards from the outer cylindrical surfaces of the drums. The drums 10 are adapted to cooperate with the web 17 passing therebetween so as to form therein uniformly distributed holes or passages 22 extending right through the web 17. The perforated web 17 is passed over a roller 23 and down into a bath 24 of a suitable curable liquid plastic material, such as a dispersion of ethylene/vinyl acetate/vinylchloride copolymer or acrylate copolymer. The web 17 is passed below a pair of rollers 25 and 26, which ensure that the web 17 is submerged into the bath 24, when passing the same. When passing the bath 24, the outer surfaces of the web 17 are coated with a layer of the curable dispersion, which also penetrates into and fills the through-going openings or passages 22. When the coated web 17 leaves the bath 24 it is passed between a pair of oppositely arranged, spring-activated rollers 27 and 28 so as to remove excess amounts of dispersion from the web 17 and return it to the bath 24. The web 17 in which the transverse passages or holes 22 are now filled with the dispersion of plastic material, and which has its opposite surfaces coated with a layer of such material, is now passed between a pair of heating devices 29 and 30 for drying the web and for curing the plastic material thereon. While passing through the heating devices 29 and 30, the web 17 is supported by the conveyor belt 19, which may, for example, have supporting belts made from wire mesh or another structure allowing heating of the lower surface of the web 17. When the web has passed the curing zone with the heating devices 29 and 30, the coating layers on the outer surfaces of the web have been hardened or cured so as to form the gas impervious cover layers 12 interconnected by connecting strings 13 extending through the openings or holes 22. The liquid plastic material applied to the web 17 is preferably of a type, which shrinks during hardening or curing, and the filtering layer 11 sandwiched between the cover layers 12 will then become compressed to some extent. The treated filter web may then be rolled up into a web roll 31. The coated web 17 may thereafter be dipped into a further bath (not shown) containing a heat sealable plastic dispersion, such as a dispersion of ethylene/vinyl acetate and thereafter dried so as to obtain an outer sealable coating or layer on the outer surfaces thereof.

Filter elements of the type shown in FIG. 1 may now be cut or punched from the finished filter web. These filter elements may have a circular outline as illustrated in FIGS. 2 and 3, and when such circular filter elements have been punched from the filter web it is only necessary to make a central opening in one of the cover layers. The filter elements may be punched from the web with any other suitable outline.

As indicated above, the filtering web 17 may comprise a matrix of a fibrous material such as cotton fibres, or other natural or synthetic fibres, and a relatively big amount of finely granulated activated carbon or another active substance may be incorporated therein without any delamination tendency of the matrix during use of the filter element. Alternatively, the matrix may be made from any other deformable porous fluid-penetrable material, such as foamed plastic or rubber.

FIG. 5 illustrates an alternative method of making a filtering element of the type shown in FIG. 1. In the method illustrated in FIG. 5 the filtering web 17 is sandwiched between a pair of plastic films 32 loosely engaged with the opposite side surface of the filtering web 17, and the web with these plastic films is passed through a space defined between a retainer plate 33 and a supporting plate 34. A moulding head 35 having a plurality of moulding spouts 36 is movable in relation to the retainer plate 33. When a section of the web 17 and the plastic films 32 have been passed into the space defined between the retainer plate 33 and the supporting plate 34, the retainer plate 33 is moved downwardly so as to slightly compress the web 17. Thereafter, the moulding head 35 having its spouts 36 extending through openings formed in the retainer plate 33, is moved downwardly, whereby the upper plastic film 28 and the web 17 is penetrated by the spout 36 till their outer ends come into contact with the lower plastic film 32. A suitable dispersion of plastic material or another liquid curable, plastic material is now ejected through the spouts 31, while the moulding head is retracted in upward direction so as to form the connecting strings 13 interconnecting the covering layers formed by the plastic films 32. When the ejected plastic material has been cured or hardened, the retainer plate 33 may be raised, and the web 17 as well as the plastic films 32 may now be moved a further step forward, whereafter the operation just described may be repeated.

FIGS. 6 and 7 illustrate a further method for making filter elements, namely elements as that shown in FIG. 8. In FIG. 6 a filter web or filter mat 37 has been cut into blanks 38, each having an arabesque-like outline, and in FIG. 6 only two such blanks, which are slightly separated from each other, are shown. Each blank 38 includes a longitudinally extending connecting strip 39 and a number of projections 40 extending transversely from the strip 39. Each of these blanks of fibrous or porous filter material may be exposed to a treatment as that illustrated in FIG. 4, whereby the outer surfaces of the blanks are coated by a cover layer 41 of a gas impervious plastic material, and the layers covering the oppositely arranged larger side surfaces of the blanks are interconnected by connecting strings 42 as previously explained.

In a succeeding operation the coated projections 40 are cut from the connecting strip 39 by means of a pair of cutting knives 43 as illustrated in FIG. 7. The end surface of the resulting filter elements 44 (shown in FIG. 8), where the filtering layer 45 is exposed, may then form a gas or fluid inlet opening, and outlet openings 46 may be provided in one of the side surfaces at the opposite end surface as illustrated in FIG. 8.

FIG. 9 illustrates an alternative method, in which the web of fibrous or porous filtering material has a width corresponding to the desired width of the final filter elements shown in FIG. 10. This narrow web or strip of filtering material is treated in an apparatus that is shown in FIG. 4, and the resulting coated strip 47, where the outer surfaces are covered by cover layers 41 and are interconnected by connecting strings, is thereafter cut into desired lengths by means of a cutting knife 48. The resulting filter elements are open at both end surfaces, and these open end surfaces may be used an inlet openings as shown in FIG. 10 and outlet openings 49 may be provided in one of the cover layers 41 at a central position.

In the drawings, the thickness of the filter webs and the filter elements have been shown with a relatively great thickness for illustrative purposes. When the filter elements are used as gas filters, for example for stoma bags, the thickness of the filter elements is normally substantially smaller compared to the other dimensions of the elements.

In the following example the production of gas filter elements for use in stoma bags of the type shown in FIGS. 2 or 3, is described.

EXAMPLE

Filter elements of the type shown in FIG. 1 for stoma bags were made by a method as that illustrated in FIG. 4 from a fibrous mat or web with a thickness of 2.5 mm. The web included an acrylic matrix, which contained a big concentration of finely granulated, superactivated carbon. This web was perforated by means of a pair of cooperating drums provided with spikes with a cross-sectional diameter of 1 mm, and the spikes were axially and peripherally spaced at distances of about 5 mm. The perforated filter web was then passed through a bath of a dispersion of ethylene/vinylacetate/vinylchloride copolyer or acrylate copolymer, which covered the surfaces of the filter web and penetrated into the perforations made therein. After drying and curing of this copolymer, the web was passed through a second bath of an ethylene/vinylacetate dispersion, which was of a type which may be heat-sealed to the walls of the plastic stoma bags in connection with which the final filter elements are to be used. The last mentioned dispersion of ethylene/vinylacetate was of the type marketed by Axo-Chemie Düren, the Federal Republic of Germany under the tradename "Ehaflex".

When the copolymer forming the connecting strings extending transversely through the perforations formed in the filter web had dried and was cured, the material shrank to some extent. This means that the filter web was compressed, so that the final thickness of the filter web was about 2 mm. Circular filter elements of the type illustrated in FIGS. 1–3 and having diameters of 30 and 40 mm, respectively, were now punched or cut from the web, and one of the cover layers of these filter elements may now be heat-sealed to the inner surface of a tube of a plastic film, which is thereafter closed to a bag by transverse welding seams. Simultaneously or subsequently, an opening corresponding to the venting opening 15 shown in FIG. 2 is formed centrally in one of the cover layers of the filter element and in the adjacent back wall to which it is welded.

In the foregoing description the filter element according to the invention has especially been described for use in connection with stoma bags. It should be understood, however, that the filter element according to the invention may also be used for various other purposes and that the active substance need not necessarily be activated carbon. As an example, instead of being used as a gas filter, the filter element according to the invention may be adapted to be used as a liquid absorbing element, for example for absorbing urine, blood, or other body liquids. In that case the active substance may, for example, be silicagel, phosphorous pentoxide, sodium polyacrylate, etc.

I claim:

1. A plate-like element for filtering a fluid flowing therethrough, said element comprising a filtering layer including a deformable porous material, a pair of cover layers covering opposite side surfaces of the filtering layer and being of a material which is substantially impervious to said fluid, and a plurality of spaced connecting strings extending transversely through the filtering layer, said connecting strings being formed from a curable liquid material which is cured in situ as integral parts of and interconnecting said opposite cover layers.

2. An element according to claim 1, wherein the filtering layer comprises a fibrous basic material carrying an active fluid component receiving substance.

3. An element according to claim 2, wherein the said active substance comprises activated carbon.

4. An element according to claim 3, wherein said filtering layer is adapted for receiving a gas.

5. An element according to claim 4 which is adapted for securement to a stoma bag to serve as a stoma bag venting filter.

6. A circular element according to claim 5, wherein the radius of the element exceeds a multiple of the thickness of the filtering layer, which is exposed at a centrally positioned opening defined in one of the opposite cover layers and at one or more openings formed at the periphery of the element.

7. An elongated element according to claim 5 with a substantially rectangular contour, wherein the opposite cover layers are fluid impervious interconnected along their longitudinal edges, while the filtering layer is exposed at both ends of the element.

8. An element according to claim 7, wherein the filtering layer is also exposed at at least one centrally located opening defined in one of the opposite cover layers.

9. An element according to claim 1, wherein the length of the connecting strings is such that the filtering layer is maintained in a compressed condition.

10. An element according to claim 1, wherein the cover layers and the interconnecting strings are made from plastic material.

11. An element according to claim 10, wherein the cover layers comprise a dispersion of ethylene/vinyl acetate/vinylchloride copolymer.

12. An element according to claim 11, wherein the connecting strings are made from a dispersion of ethylene/vinylacetate/vinylchloride copolymer.

13. An element according to claim 1, wherein the cover layers are flexible film-like layers.

14. An element according to claim 13, wherein the inner surfaces of the cover layers are adhered to the adjacent surfaces of the filtering layer.

15. An element according to claim 13, wherein the opposite cover layers are formed in situ from said curable liquid material.

* * * * *

UNITED STATES PATENT AND TRADEMARK OFFICE
CERTIFICATE OF CORRECTION

PATENT NO. : 4,579,658
DATED : April 1, 1986
INVENTOR(S) : Klaus Moller

It is certified that error appears in the above-identified patent and that said Letters Patent are hereby corrected as shown below:

On the title page insert

-- [73] Assignee: Dansac A/S
Fredensborg, Denmark --.

Signed and Sealed this

Fifth Day of August 1986

[SEAL]

Attest:

DONALD J. QUIGG

Attesting Officer

Commissioner of Patents and Trademarks